United States Patent [19]
Marks

[11] Patent Number: 5,122,115
[45] Date of Patent: Jun. 16, 1992

[54] MULTILUMEN ANGIOGRAPHY CATHETER

[75] Inventor: Lloyd A. Marks, Bryn Mawr, Pa.

[73] Assignee: Temple University, Philadelphia, Pa.

[21] Appl. No.: 447,717

[22] Filed: Dec. 8, 1989

[51] Int. Cl.⁵ ............................................. A61M 25/00
[52] U.S. Cl. ..................................... 604/53; 128/658; 604/101; 604/280
[58] Field of Search ................ 604/53, 96, 101, 102, 604/280, 281; 128/656, 658; 606/194

[56] References Cited

U.S. PATENT DOCUMENTS

| | | | |
|---|---|---|---|
| 4,453,545 | 6/1984 | Inoue | 604/101 |
| 4,581,017 | 4/1986 | Sahota | 604/102 |
| 4,689,041 | 8/1987 | Corday et al. | 604/96 |
| 4,714,460 | 12/1987 | Calderon | 604/53 |
| 4,822,345 | 4/1989 | Danforth | 606/194 |
| 4,832,028 | 5/1989 | Patel | 604/101 |
| 4,862,874 | 9/1989 | Kellner | 604/96 |
| 4,883,459 | 11/1989 | Calderon | 128/656 |
| 4,909,258 | 3/1990 | Kuntz et al. | 128/658 |
| 4,983,166 | 1/1991 | Yamawaki | 606/194 |

Primary Examiner—Stephen C. Pellegrino
Assistant Examiner—Ralph A. Lewis
Attorney, Agent, or Firm—Ratner & Prestia

[57] ABSTRACT

A multiple lumen catheter specifically adapted for selective visualization of one or the other of the coronary arteries. One lumen of the multiple lumen catheter is adapted to deliver contrast agent to the coronary artery to be visualized while a second, and optionally a third, lumen is adapted to limit flow of contrast agent to one or more other locations in the aortic root complex. The invention also includes a method of preparing for coronary angiography using such a catheter.

2 Claims, 4 Drawing Sheets

MULTILUMEN ANGIOGRAPHY CATHETER

FIELD OF THE INVENTION

The invention relates to catheters and methods in which such catheters are used in cardiology and specifically to apparatus and methods used for selective imaging in coronary angiography.

BACKGROUND OF THE INVENTION

A diagnostic test used in cardiology is aortography wherein contrast agent is injected into the aortic root and subsequently into the coronary arteries while an image is taken. In this procedure, a large bolus of contrast agent is injected into the aortic root complex which branches into the right coronary artery (RCA) and the left coronary artery (LCA). In certain angled views, the images of these vessels may overlay each other, however, causing difficulty in their detailed visualization.

Accordingly, selective coronary angiography is a standard practice in cardiology. In this method, specially designed catheters are used to seek out the RCA and LCA for the direct injection of contrast agent. Two separate catheters must be used, with the LCA generally being easier to cannulate. Either coronary artery may present difficulty in cannulation.

BRIEF DESCRIPTION OF THE INVENTION

In the present invention, there is provided a multiple lumen catheter specifically adapted for selective visualization of one or the other of the coronary arteries. This catheter includes one lumen adapted to deliver contrast agent to a selected location in the aortic root complex and a second lumen adapted to limit flow of contrast agent to another selected location in the aortic root complex, either by delivery of a non-contrasting fluid, such as blood, or by deployment of a balloon.

The invention also includes a method of preparing for coronary angiography by manipulating the distal end of a multiple lumen catheter into the aortic root complex, positioning one lumen thereof in a coronary artery and delivering non-contrast agent therethrough while positioning the second lumen in the aortic root complex and delivering contrast agent therethrough. Furthermore, the method of preparing for coronary angiography may also include deploying a balloon to limit passage of contrast agent into the ascending aorta or one of the coronary arteries.

DETAILED DESCRIPTION OF THE INVENTION

In the heart, the aortic root complex is the space below the ascending aorta and above the aortic valve and left ventricle. The aortic root complex includes openings into the left coronary artery (LCA) and the right coronary artery (RCA) just below the ascending aorta. The present invention comprises apparatus and methods for coronary angiography involving manipulations in the aortic root complex to selectively image parts of that complex and/or the coronary arteries.

Figure 1:
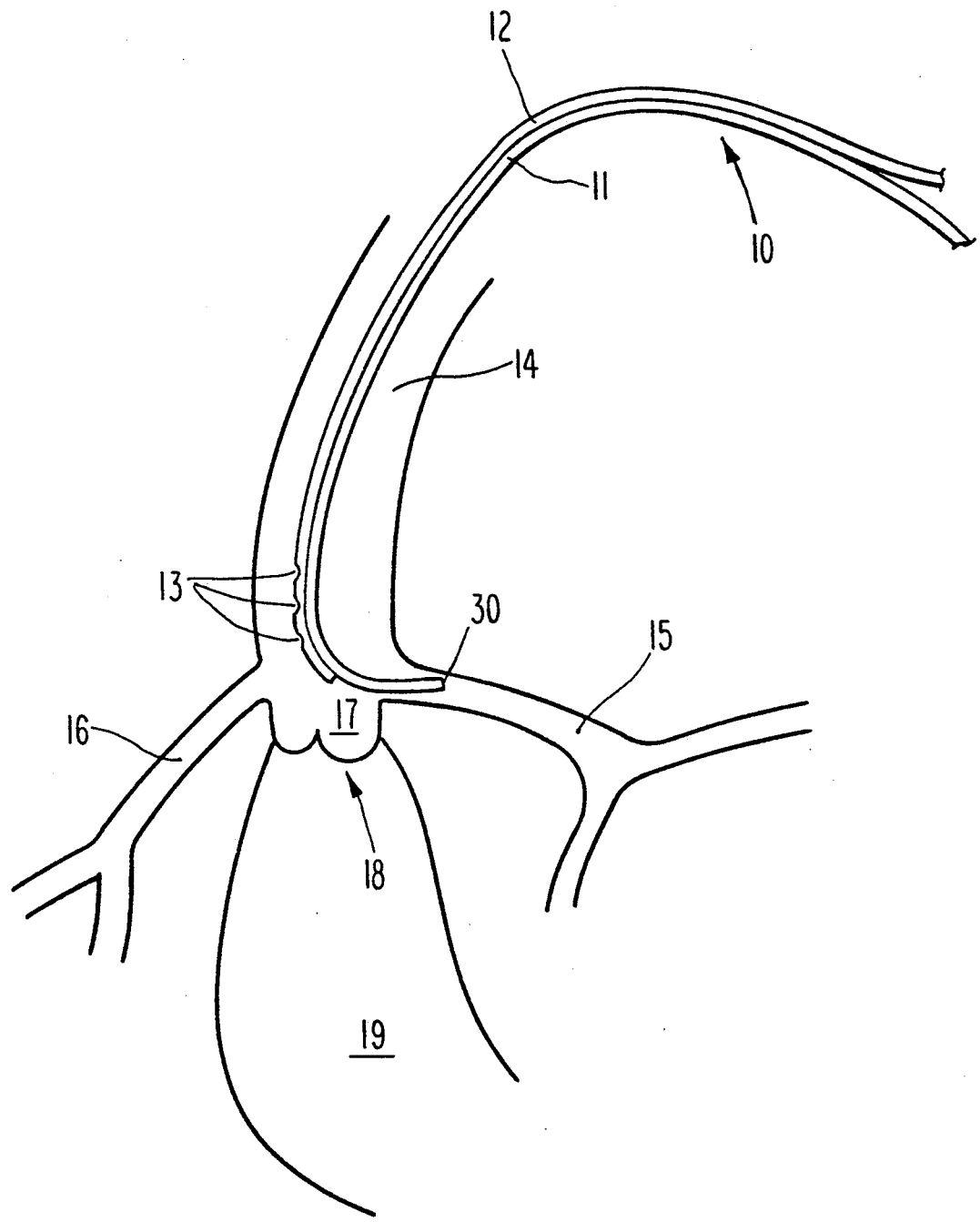
FIG. 1 illustrates a double lumen coronary catheter as used in accordance with the present invention.

As shown in FIG. 1, in one embodiment, the present invention comprises a catheter 10, adapted to be inserted though ascending aorta 14 and manipulated into the aortic root complex 17. Catheter 10 includes a first lumen 12, adapted to be positioned in aortic root 17, above aortic valve 18 and left ventricle 19. Catheter 10 also includes a second lumen 11 with distal opening 30, adapted to be positioned in LCA 15. Lumen 12 includes pores 13 in its outer wall.

Figure 2:
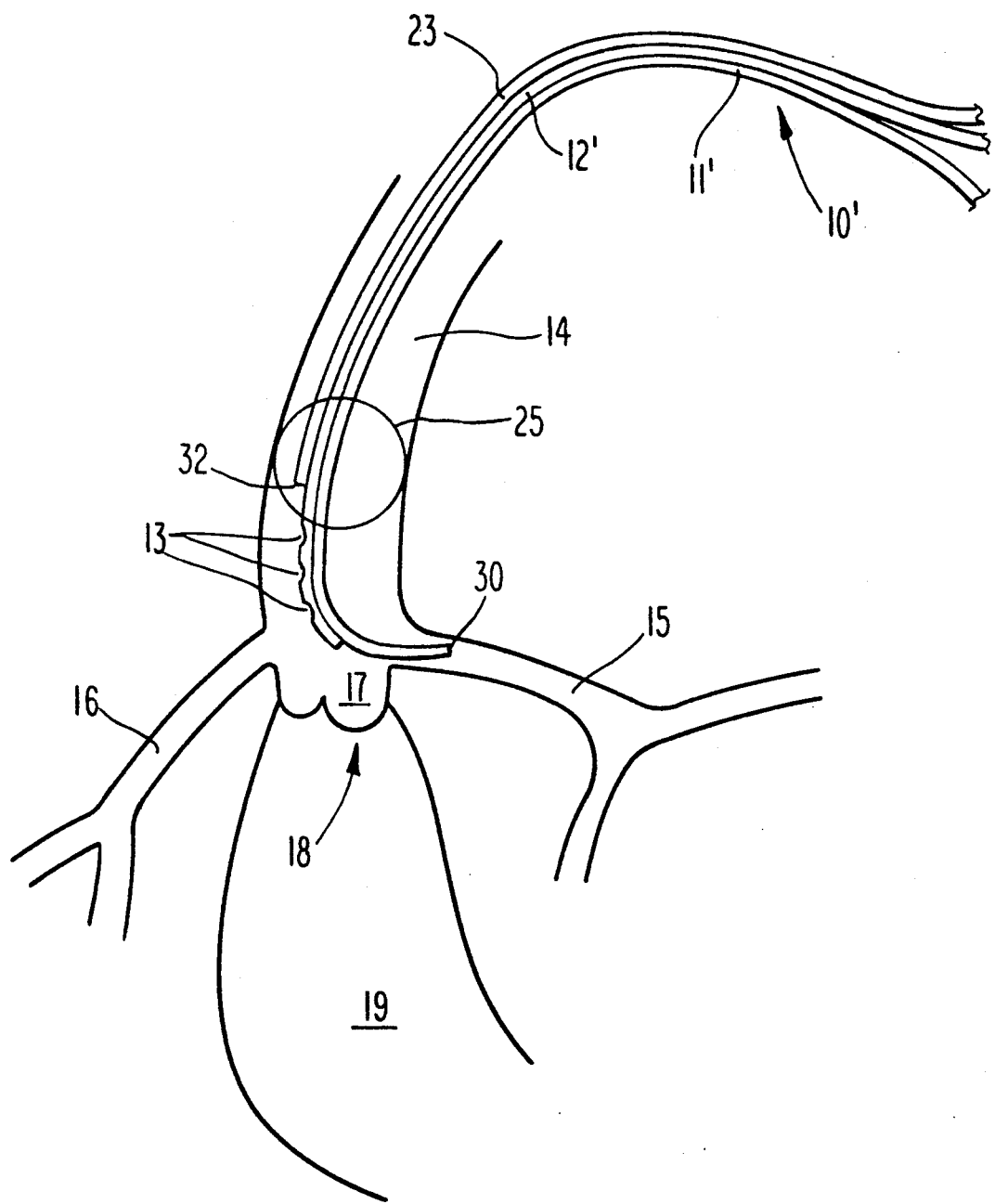
FIG. 2 illustrates a triple lumen coronary catheter as used in accordance with the present invention.

As shown in FIG. 2, another embodiment of the invention comprises catheter 10', adapted to be inserted through ascending aorta 14 and manipulated into the aortic root complex 17. Catheter 10' includes a first lumen 12', adapted to be positioned in aortic root 17. A second lumen, 11', with distal opening 30 of catheter 10' is adapted to be positioned in LCA 15. Catheter 10' also includes a third lumen 23 with distal opening 32, adapted to deploy balloon 25 above the aortic root 17 and below ascending aorta 14.

As the embodiment of FIG. 1 is typically used, also in accordance with another aspect of the present invention, contrast agent is directed into the aortic root 17 via pores 13 of lumen 12 as a non-contrast agent (preferably the patient's own blood) is directed into LCA 15 via distal opening 30 of lumen 11 of catheter 10. This effectively blocks contrast agent from LCA 15, since LCA 15 is filled with blood. The aortic root complex is thus prepared for selective radiographic visualization of the RCA, distinct from the LCA, by virtue of the exclusion of contrast agent from the LCA by the simultaneous delivery of non-contrast agent therein.

As the embodiment of FIG. 2 is used, also in accordance with another aspect of the present invention, contrast agent is directed into aortic root 17 via pores 13 of lumen 12' of catheter 10' as non-contrast agent (preferably the patient's own blood) is directed into the LCA 15 via distal opening 30. Furthermore, lumen 23 is adapted to deploy a balloon 25 above aortic root 17 and below the ascending aorta 14. This balloon 25, upon inflation by passing gas or a liquid through lumen 23 and out through distal opening 32, for example, effectively confines contrast agent to the aortic root complex since balloon 25 blocks the diameter of ascending aorta 14. The aortic root complex is thus prepared for selective radiographic visualization of the RCA, distinct from the LCA by the simultaneous delivery of non-contrast agent therein which excludes contrast agent from the LCA.

Figure 3:
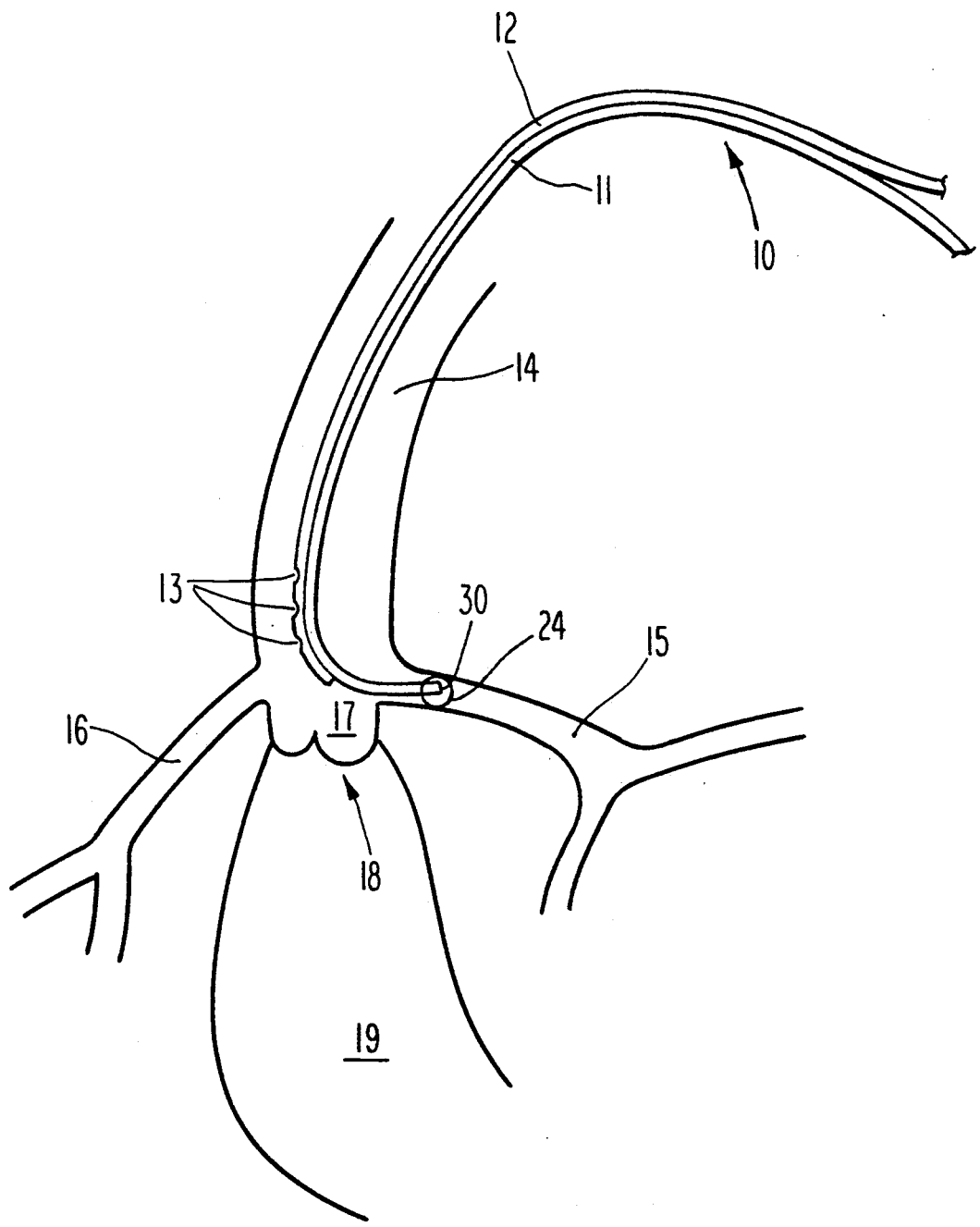
FIG. 3 illustrates an alternative embodiment of a double lumen coronary catheter of FIG. 1 as used in accordance with the claimed invention.
Figure 4:
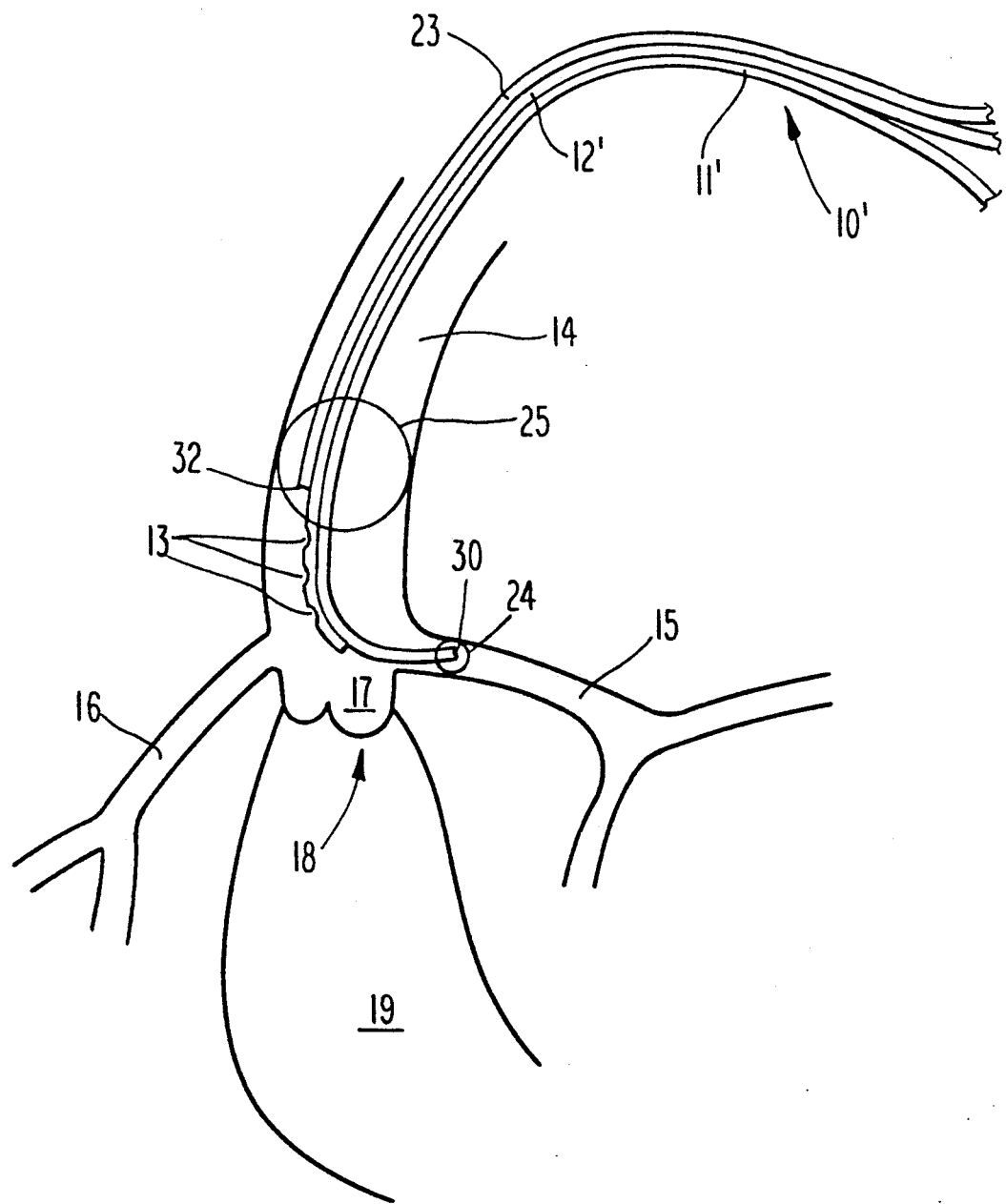
FIG. 4 illustrates an alternative embodiment of a double lumen coronary catheter of FIG. 2 as used in accordance with the claimed invention.

In an alternative embodiment lumen 11 (in FIG. 3) or 11' (in FIG. 4) may be used to deploy balloon 24, rather than to inject a non-contrast agent, and thereby, upon inflation of the balloon associated with lumen 11 or 11' via distal opening 30, limit flow of contrast agent into LCA 15.

In another alternative embodiment, catheters 10 or 10', in the embodiments of FIGS. 1 and 2 respectively, may be adapted for selective visualization of the LCA (rather than the RCA) by inclusion of a modified form of lumen 11 or 11' adapted for easy placement into RCA 16 rather than LCA 15

As will be obvious to those skilled in the art, the special purpose catheter of this invention may also be used in a conventional manner for selective coronary angiography, that is by injecting contrast agent in a selected location without simultaneously preventing entry of the contrast agent in non-selected locations.

In those embodiments in which a balloon is used selectively to occlude a coronary artery, means (possibly an additional lumen parallel to lumen 11) for accommodating a guide wire may optionally be included, to facilitate proper positioning of the catheter of this invention. Such a guide wire may be positioned in a coronary artery through a conventional coronary seeking catheter. Once the wire is in place, the conventional catheter is then removed over the wire. The catheter 10 or 10' is then positioned in the coronary artery using the wire as a guide.

While this invention has been disclosed with reference to specific embodiments, it is apparent that other embodiments and equivalent variations of this invention may be devised by those skilled in the art without departing from the true spirit and scope of this invention. The appended claims are intended to be construed to include all such embodiments and equivalent variations.

What is claimed is:

1. A method of preparing for coronary angiography comprising manipulating a multiple lumen catheter, having a first lumen with a distal opening and a second lumen with pores, until the distal end of said catheter is placed in the aortic root complex, positioning said first lumen in a coronary artery not to be imaged while said second lumen remains in the aortic root complex, delivering a non-contrast agent through said distal opening to the coronary artery not to be imaged, and delivering contract agent through said pores to the coronary artery to be imaged.

2. A method of preparing for coronary angiography, as recited in claim 1, wherein said catheter includes a third lumen having a distal opening and outer walls and including a means to block the ascending aorta.

* * * * *

UNITED STATES PATENT AND TRADEMARK OFFICE
CERTIFICATE OF CORRECTION

PATENT NO. : 5,122,115
DATED : June 16, 1992
INVENTOR(S) : Lloyd A. Marks

It is certified that error appears in the above—identified patent and that said Letters Patent is hereby corrected as shown below:

Column 4, Claim 1, line 14, delete "contract" and insert therefor
--contrast--.

Signed and Sealed this

Sixteenth Day of August, 1994

Attest:

BRUCE LEHMAN

Attesting Officer

Commissioner of Patents and Trademarks